United States Patent
Nagano et al.

(10) Patent No.: US 11,111,434 B2
(45) Date of Patent: Sep. 7, 2021

(54) LIGHT EMITTER, METHOD FOR PRODUCING LIGHT EMITTER, AND BIOLOGICAL SUBSTANCE LABELING AGENT

(71) Applicant: Murata Manufacturing Co., Ltd., Nagaokakyo (JP)

(72) Inventors: Takahito Nagano, Nagaokakyo (JP); Norikazu Fujihira, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 123 days.

(21) Appl. No.: 16/007,118

(22) Filed: Jun. 13, 2018

(65) Prior Publication Data

US 2018/0291267 A1    Oct. 11, 2018

Related U.S. Application Data

(63) Continuation of application No. PCT/JP2016/078513, filed on Sep. 27, 2016.

(30) Foreign Application Priority Data

Jan. 19, 2016 (JP) .............................. JP2016-007856

(51) Int. Cl.
| | |
|---|---|
| *C09K 11/88* | (2006.01) |
| *A61K 49/00* | (2006.01) |
| *B82Y 40/00* | (2011.01) |
| *B82Y 5/00* | (2011.01) |
| *B82Y 30/00* | (2011.01) |
| *B82Y 20/00* | (2011.01) |
| *B82Y 15/00* | (2011.01) |

(52) U.S. Cl.
CPC .......... *C09K 11/88* (2013.01); *A61K 49/0019* (2013.01); *A61K 49/0065* (2013.01); *B82Y 40/00* (2013.01); *B82Y 5/00* (2013.01); *B82Y 15/00* (2013.01); *B82Y 20/00* (2013.01); *B82Y 30/00* (2013.01); *Y10S 977/773* (2013.01); *Y10S 977/896* (2013.01); *Y10S 977/927* (2013.01)

(58) Field of Classification Search
CPC ................ C09K 11/88; A61K 49/0019; A61K 49/0065; B82Y 40/00; B82Y 5/00; B82Y 15/00; B82Y 20/00; B82Y 30/00; Y10S 977/773; Y10S 977/896; Y10S 977/927
See application file for complete search history.

(56) References Cited

U.S. PATENT DOCUMENTS

| | | | |
|---|---|---|---|
| 2007/0205416 A1 | 9/2007 | Sakata et al. | |
| 2009/0159849 A1 | 6/2009 | Uehara et al. | |
| 2014/0020738 A1 | 1/2014 | Aida et al. | |
| 2014/0326949 A1* | 11/2014 | Xu ........................ | C09K 11/02 257/13 |

FOREIGN PATENT DOCUMENTS

| | | |
|---|---|---|
| CN | 104513664 A | 4/2015 |
| CN | 105154084 A | 12/2015 |
| JP | 2007169605 A | 7/2007 |
| JP | 2007265974 A | 10/2007 |
| JP | 2012222006 A | 11/2012 |

OTHER PUBLICATIONS

International Search Report issued for PCT/JP2016/07851, dated Nov. 15, 2016.
Written Opinion of the International Searching Authority issued for PCT/JP2016/078513, dated Nov. 15, 2016.
S. Ozaki et al.; "Optical absorption and photoluminescence in the ternary chalcopyrite semiconductor AgInSe2"; Journal of Applied Physics, 100, 2006, 113526-1-113526-8.
T. Omata et al.; "Size dependent optical band gap of ternary I-III-VI2 semiconductor nanocrystals"; Journal of Applied Physics, 105, 2009, 073106-1-073106-5.
O. Yarema et al.; "Independent Composition and Size Control for Highly Luminescent Indium-Rich Silver Indium Selenide Nanocrystals"; ACS Nano, 2015, vol. 9, No. 11, pp. 11134-11142.
M.A. Langevin et al.: "Air-Stable Near-infrared AgInSe2 Nanacrystals"; ACS Nano, 2014, vol. 8, No. 4, pp. 3476-3482.
Y. Jin et al.; "Hydrothermal synthesis and characterization of AgInSe2 nanorods"; Journal of Crystal Growth, 253, 2003, pp. 429-434.
Yao, D et al.; "Phosphine-free-synthesis of Ag—In—Se alloy nanocrystals with visible emissions"; Nanoscale, 2015, vol. 7, No. 44, p. 18570-18578. (Supporting information: Phosphine-free-synthesis of Ag—In—Se alloy nanocrystals with visible emission, 9 pages).

\* cited by examiner

*Primary Examiner* — Robert S Cabral
(74) *Attorney, Agent, or Firm* — Arent Fox LLP

(57) ABSTRACT

A light emitter is formed from nanoparticles including a compound semiconductor containing an Ag component, In component, and Se component. The peak wavelength of the emission intensity falls within the range of 700 to 1400 nm, and the half-value width ΔH for the peak wavelength is 100 nm or less. The light emitted is configured to emit strong light in the near-infrared region, and which is capable of detecting biological information, and is preferred for bio-imaging.

6 Claims, 13 Drawing Sheets

LIGHT EMITTER, METHOD FOR PRODUCING LIGHT EMITTER, AND BIOLOGICAL SUBSTANCE LABELING AGENT

CROSS REFERENCE TO RELATED APPLICATIONS

The present application is a continuation of PCT/JP2016/078513 filed Sep. 27, 2016, which claims priority to Japanese Patent Application No. 2016-007856, filed Jan. 19, 2016, the entire contents of each of which are incorporated herein by reference.

TECHNICAL FIELD

The present disclosure relates to a light emitter, a method for producing a light emitter, and a biological substance labeling agent. More particularly, the present disclosure relates to a light emitter suitable for a label (biomarker) for a biological substance constituting a living body, a method for producing the light emitted, and a biological substance labeling agent including the light emitter.

BACKGROUND

In recent years, in the biomedical field, bioimaging techniques have been attracting attention for giving fluorescence to biological substances and then dynamically analyzing images with high sensitivity and multiple colors, and confirming medication effects and cell states in regenerative medicine, cancer therapy, or the like. The bioimaging techniques adsorb, to living tissues, light emitters composed of ultrafine semiconductor nanoparticles subjected to ultrafine atomization, irradiate the light emitters with light to cause the light emitters to emit light, and detect biological information. Therefore, as compared with PET (Positron Emission Tomography) or CT (Computed Tomography), simpler and safer medical examinations are expected to be achieved, because the states of the biological substances can be confirmed just by irradiating the light emitters in the living body with light.

In this type of bioimaging technique, it is conventionally considered preferable to use a light emitter that produces a fluorescence phenomenon in the near-infrared region of 700 to 1700 nm in wavelength. More specifically, biological constituent substances, such as hemoglobin, are highly absorbent in the visible light region from 400 nm to shorter than 700 nm, which is shorter in wavelength than the near-infrared region. In addition, when the wavelength is longer than 1700 nm, moisture absorption is increased, thereby making it difficult for light to pass through the living body with high efficiency. In contrast, the near-infrared region of 700 to 1700 nm is high in light transmittance in living bodies, and thus considered suitable for bioimaging techniques. In particular, the range of 700 to 900 nm and 1200 to 1500 nm in wavelength is favorable in light transmittance, and referred to as a "biological window".

On the other hand, semiconductor nanoparticles have been actively researched and developed in various technical fields, and above all, compound semiconductors that have a chalcopyrite-type crystal structure composed of Group I-III-VI elements are direct transition-type semiconductors in which through light absorption, electrons and holes are recombined to produce luminescence, which are considered promising as a novel functional materials, because the semiconductors contain harmful elements such as Cd, and have low environmental load with low toxicity.

As prior art documents on this type of compound semiconductor, for example, Non-Patent Documents 1 to 3 and Patent Document 1 (identified below) are known.

For example, Non-Patent document 1 is related to light absorption and fluorescence in ternary chalcopyrite semiconductor $AgInSe_2$. Moreover, according to Non-Patent Document 1, the absorption energy of $AgInSe_2$ depends on temperature, with bandgap energy of 1.222 eV at a temperature of 13 K, and 1.229 eV at a temperature of 100 K (same document, FIG. 1), and that the emission intensity reaches a peak with bandgap energy of about 1.175 eV (about 1055 nm in terms of wavelength), but decreases with increase in temperature, and produces almost no luminescence at a temperature of 60 K (same document, FIG. 5).

In addition, Non-Patent Document 2 indicates an optical band gap that depends on the particle sizes of ternary $I-III-VI_2$ semiconductor nanocrystals.

Yet further, according to Non-Patent Document 2, when the relationship between the particle size and bandgap energy of $CuInS_2$ is calculated with the use of finite-depth-well effective mass approximation calculation (hereinafter referred to as a "FDW-EMA method"), the calculation result corresponds approximately to the experimental result (same document, FIG. 2). In addition, for six types of $I-III-VI_2$ compound semiconductor nanoparticles of: $CuInSe_2$, $CuGaS_2$, $CuGaSe_2$, $AgInSe_2$, $AgGaS_2$, and $AgGaSe_2$, the relationship between the particle size and the bandgap energy is simulated with the use of the FDW-EMA method, thereby estimating the emission wavelength region (same document, FIGS. 3 and 4).

Further, it is reported that even when the respective compound semiconductors mentioned above have the same component compositions, varying the particle sizes can achieve different levels of bandgap energy in a wide wavelength region from near infrared to ultraviolet. For example, in the case of $AgInSe_2$, it is described that the bandgap energy is about 1.5 eV (about 826.7 nm in terms of wavelength) when the particle size is 6 nm, but the bandgap energy is increased as the particle size is reduced, and the bandgap energy is about 3.38 eV (about 366.9 nm in terms of wavelength) when the particle size becomes 1 nm.

More specifically, in general, semiconductor nanoparticles subjected to ultrafine atomization down to an average particle size of about 10 nm or less exhibit the quantum size effect of increasing the bandgap energy with reduction in particle size, and even when a semiconductor material is used which has the same component composition, the light absorption/emission wavelength can be controlled over a wide range. Further, in Non-Patent Document 2, for the above-described seven types of compound semiconductors, it is predicted that, due to the quantum size effect, the emission wavelengths can be changed by varying the particle sizes.

In addition, Non-Patent Document 3 indicates independent composition and particle size control for highly fluorescent In-rich Ag—In—Se nanocrystals.

That is, according to Non-Patent Document 3, Ag—In—Se based semiconductor nanoparticles are synthesized with the use of an amide acceleration synthesis method. More specifically, first, AgI and $InI_3$ are dissolved in trioctylphosphine (TOP), and heated to 260° C., thereby preparing an Ag—In precursor solution. Next, a mixed solution of Se and an amide compound $LiN(Si(CH_3)_3)_2$ dissolved in TOP is poured into the Ag—In precursor solution to develop a reaction for 15 to 120 seconds, which is followed by a predetermined post-treatment, thereby synthesizing various Ag—In—Se based nanoparticles combined so as to be rich in In in the Ag/In range of 0.1 to 0.8.

According to Non-Patent Document 3, luminescence is produced with a donor-accepter pair (hereinafter referred to as a "DAP"), for which an electron captured at the donor level and a hole captured at the acceptor level form a pair for recombination, and Ag—In—Se based nanoparticles are obtained, where the quantum yield is 24% in the case of $AgIn_3Se_5$, and 73% in the case of a core-shell structure of $Ag_3In_5Se_9$ as a core part and ZnSe as a shell part (same document, Table 1).

Further, according to Non-Patent Document 3 herein, Ag—Ig—Se based compound semiconductor nanoparticles are obtained, where the Stokes shift indicating the deviation between the absorption wavelength and the emission wavelength is 200 to 260 nm, and the full width at half maximum (FWHM (full width at half maximum); hereinafter, referred to simply as a "half-value width") at the peak wavelength of the emission intensity is 180 to 260 nm (same document, FIG. 4).

In addition, Patent Document 1 proposes a fluorescent body of a first compound containing one element from each of the I-III-VI Groups has a chalcopyrite structure, where particles of the first compound have an outer diameter of 0.5 to 20.0 nm, and a the fluorescence quantum yield of emitting a light wave excited by excitation light is 3.0% or more and 20.0% or less at room temperature.

Furthermore, Patent Document 1 herein describes containing Cu or Ag as a Group I element, In or Ga as a Group III element, and S or Se as a Group VI element.

Further, according to Patent Document 1, a solution of CuI and $InI_3$ dissolved in oleylamine as a complexing agent is defined as solution A, a solution of thioacetamide to serve as an S source dissolved in TOP is defined as solution C, the solution A and a solution C are mixed, and the mixed solution is aged at 25° C. for 24 hours or 28 days under an argon atmosphere, and then heated at a temperature of 160 to 280° C. for 3 to 600 seconds to develop a reaction, thereby synthesizing Cu—In—S based compound semiconductors of multiple compositions that differ in the combination ratio between Cu and In.

Further, Patent Document 1 herein describes emission spectra in the case of varying the aging time, the heating temperature after aging, the heating time, the wavelength of excitation light, and the Cu/In ratio, which achieve emission characteristics of 650 to 700 nm in peak wavelength and on the order of 150 nm in half-value width.

Furthermore, Patent Document 1 herein also describes examples of adding Ga or Ag to a Cu—In—S based compound, where for example, $AgInS_2$ that uses Ag instead of Cu achieves emission characteristics of about 750 nm in peak wavelength and on the order of 110 nm in half-value width maximum are obtained.

Patent Document 1: Japanese Patent Application Laid-Open No. 2007-169605.

Non-Patent Document 1: S. Ozaki et al., "Optical absorption and photoluminescence in the ternary chalcopyrite semiconductor AgInSe2", J. Appl. Phys. 100, 113526-1-113526-8, 2006.

Non-Patent Document 2: T. Omata et al., "Size dependent optical band gap of ternary I-III-VI2 semiconductor nanocrystals", J. Appl. Phys. 105, 073106-1-073106-5, 2009.

Non-Patent Document 3: O. Yarema et al., "Independent Composition and Size Control for Highly Luminescent Indium-Rich Silver Indium Selenide Nanocrystals" ACS Nano, Article ASAP.

However, while Non-Patent Document 1 discloses emission characteristics of a bulk $AgInSe_2$ compound semiconductor, Non-Patent Document 1 fails to describe emission characteristics of nanoparticles. More specifically, nanoparticles subjected to ultrafine atomization are believed to exhibit unique characteristics different from bulk crystals due to the quantum size effect, but according to Non-Patent Document 1, the emission characteristics of bulk crystals are evaluated at extremely low temperatures, and moreover, quenching of luminescence is caused at 60 K (—about 213° C.), without any light emitted at room temperature.

Furthermore, in Non-Patent Document 2, where the I-III-$VI_2$ compound semiconductor produces a quantum size effect with ultrafine nanoparticles of 6 nm or less, predicts the wavelength region of the emission wavelength, but fails to describe the profile of an emission spectrum.

More specifically, in order to obtain a high resolution and a large amount of biological information by the bioimaging technique, it is desirable to emit strong light in the near-infrared region of 700 nm to 1400 nm, including the "biological window", and obtain a large volume of light emission information, and to that end, it is necessary to make the peak wavelength of the emission intensity steep and sharp, thereby increasing the resolution. However, while Non-Patent Document 2 discloses the quantum size effect of the semiconductor nanoparticles, Non-Patent Document 2 fails to describe the profile of an emission spectrum, and thus fails to predict the emission characteristics required by the bioimaging technique.

In addition, according to Non-Patent Literature 3, the quantum yield is favorable, but the half-value width is a large as 180 to 260 nm, the peak wavelength is gentle with the lack of steepness/sharpness, the resolution is thus inferior, and it is difficult to obtain a large volume of biological information with high resolution desired.

More specifically, Non-Patent Document 3 relates to DAP luminescence, where the Stokes shift is as large as 200 to 260 nm, and electrons that absorb light are believed to transit from the donor level to the acceptor level through the defect level derived from a crystal structure defect. Therefore, since the transition from the absorption wavelength to the emission wavelength is believed to be accompanied by the energy loss derived from the defect level, the peak wavelength lacks steepness and sharpness, and for this reason, the full width at half maximum is increased as described above, and it is thus difficult to emit strong light at the emission wavelength.

In addition, according to Patent Document 1, Cu-based compound semiconductor nanoparticles emit light in the visible light region of 700 nm or less in wavelength, and moreover, the emission wavelength is as wide as on the order of 150 nm, and even in the case of application to the bioimaging technique, it is difficult to obtain a large volume of biological information which has a desired high resolution in a wavelength region in which the light transmittance in living bodies is favorable.

In addition, although Patent Document 1 describes the emission characteristics of $AgInS_2$, $AgInS_2$ has large bandgap energy of 1.87 eV (660 nm in terms of wavelength) in the bulk state. For this reason, when the particle size is varied on the nano level, it is believed that the bandgap energy is further increased due to the quantum size effect, thereby making light more likely to be emitted on the visible light region side, and the AgInS$_2$ is thus not suitable as a light emitter for bioimaging.

SUMMARY OF THE INVENTION

The present disclosure has been made in view of the foregoing circumstances. Thus, according to an exemplary aspect, a light emitter is disclosed that emits strong light in the near-infrared region, and which is capable of detecting a lot of biological information, and preferred for bioimaging, and a method for producing the light emitter, as well as a biological substance labeling agent including light emitter.

Ag—In—Se type compound semiconductors that have a chalcopyrite crystal structure of using Ag for a group I element, In for a group III element, and Se for a group VI element are non-toxic unlike the Cd types, and capable of producing luminescence in the near-infrared region in a bulk state. For example, AgInS$_2$ that uses S as a Group VI element has bandgap energy of 1.87 eV (660 nm in terms of wavelength) in a bulk state, and produces luminescence in the visible light region, whereas AgInSe$_2$ has bandgap energy of 1.24 eV (1000 nm in terms of wavelength) in a bulk state, and produces luminescence in the near-infrared region. Therefore, controlling the particle sizes by making the Ag—In—Se based compound semiconductors into nanoparticles is believed to be capable of achieving, due to the quantum size effect, light emitters that have different peak wavelengths in the near-infrared region of 700 to 1400 nm in wavelength, including the "biological window", even in the case of the same composition.

On the other hand, in bioimaging technology, it is necessary for a light emitter to have a favorable resolution for obtaining more effective biological information, and to that end, the peak wavelength of the emission intensity is desirably steep and sharp.

From the foregoing perspective, the inventors have focused attention on Ag—In—Se based compound semiconductors to determine that devising the production process or the like makes it possible to achieve a light emitter configured to keep the half-value width for the peak wavelength down to 100 nm or less, with the peak wavelength of the emission intensity in the range of 700 to 1400 nm, thereby making the emission spectrum near the peak wavelength steep and sharp in the near-infrared region, producing strong luminescence, and thus a desirable light emitter with a favorable resolution, which is suitable for a biomarker.

The present disclosure has been made on the basis of the foregoing finding, and a light emitter disclosed herein is formed from nanoparticles including a compound semiconductor containing an Ag compound, an In component, and a Se component, and characterized in that the peak wavelength of the emission intensity falls within the range of 700 nm to 1400 nm, and the peak wavelength is 100 nm or less in half-value width.

In addition, in the light emitted according to the present disclosure, the peak wavelength is preferably 700 nm to 1000 nm.

Thus, the half-value width for the peak wavelength can be kept down to 100 nm or less in the wavelength range referred to as a "biological window", for particularly favorable light transmittance in a living body, and a light emitter can be obtained which is more suitable for use in bioimaging.

In addition, the light emitter according to the present disclosure preferably contains the In component in excess with respect to the stoichiometric composition.

This In-rich composition makes it possible to obtain more favorable emission characteristics, since the non-radiative deactivation process is believed to be suppressed in the absorption-emission process.

Furthermore, in the light emitter according to the present disclosure, the combination ratio of the In component to the Ag component is preferably 1.5 to 3 in terms of molar ratio.

Thus, a high-purity light emitter favorable emission characteristics can be obtained, for which impurities such as different phases are prevented from being produced in the production process.

In addition, in the light emitter according to the present disclosure, the absorption wavelength preferably includes at least a part of 700 nm to 1000 nm.

Thus, it becomes possible to reduce the Stokes shift indicating the deviation between the absorption wavelength and the emission wavelength, thereby making it possible to obtain a light emitter capable of band-edge luminescence with energy loss reduced.

In the light emitter according to the present disclosure, the compound semiconductor preferably has an average particle size of 0.1 nm to 20 nm.

As described above, the compound semiconductor subjected to ultrafine atomization to the nanometer level exhibits the quantum size effect, thus making it possible to control the bandgap energy just by adjusting the particle size even in the case of the same component composition. Therefore, multiple emission characteristics that differ in the peak wavelength of the emission intensity can be obtained with the same component composition, thus allowing the detection of various biological information.

In addition, a method for producing a light emitter including, as a light emitter, a nanoparticle comprising a compound semiconductor containing an Ag component, an In component, and a Se component is disclosed that includes preparing an Ag—In precursor solution by dissolving an Ag compound and an In compound in a high boiling point solvent; preparing a Se precursor solution by dissolving Se powder in a solvent; preparing a mixed solution by injecting the Se precursor solution into the Ag—In precursor solution, with the Ag—In precursor solution heated to a predetermined temperature; and heating the mixed solution at a reaction temperature higher than the predetermined temperature for a predetermined period of reaction time.

In this aspect, the compound semiconductor is prepared at the predetermined temperature, and then heated at the reaction temperature higher than the predetermined temperature for the predetermined period of reaction time, thereby improving the crystallinity of the nanoparticles, and thus suppressing the defect generation of the nanoparticles. More specifically, the improved crystallinity reduces the variation in average grain size, and allows for the reduction of the energy loss derived from the defect level, thereby making it possible to obtain, with high efficiency, a light emitter capable of band-edge luminescence with a small half-value width and a small Stokes shift.

In the method for producing a light-emitter according to the present disclosure, the reaction temperature is preferably 200° C. or higher.

In addition, in the method for producing a light emitter according to the present disclosure, the absorption wavelength can be controlled by adjusting the combination ratio between the Ag compound and the In compound.

Thus, the Stokes shift can be adjusted, thereby making it possible to adjust the peak wavelength of the emission intensity and the half-value width.

In addition, the method for producing a light emitter according to the present disclosure can adjust the predetermined period of reaction time to control the peak wavelength of the emission intensity.

More specifically, the reaction time is adjusted, thereby making it possible to control how grain growth of the compound semiconductor is promoted, and thus produce light emitters of nanoparticles that differ in average grain size.

In addition, the method for producing a light emitter according to the present disclosure can adjust the reaction temperature to control the half-value width for the peak wavelength.

Yet further, the adjustment of the reaction temperature can also control the crystallinity of the nanoparticles, and thus control the generation of defects in the crystal structure, thus allowing the control of the half-value width for the peak wavelength.

In addition, in the method for producing a light emitter according to the present disclosure, the high boiling point solvent preferably includes at least one selected from octadecene, oleylamine and n-octyl ether.

Furthermore, in the method for producing a light emitter according to the present disclosure, the Ag compound and the In compound are complexes with a carboxylate ion as a ligand.

In addition, a biological substance labeling agent according to the present disclosure is characterized by including the light emitter described above.

In view of the foregoing, according to the present disclosure, a light emitter is disclosed that is formed from ultrafine particles including a compound semiconductor containing an Ag compound, an In component, and a Se component, with the peak wavelength of the emission intensity falling within the range of 700 nm to 1400 nm, and the peak wavelength being 100 nm or less in half-value width. Thus, in the near-infrared region, the emission spectrum near the peak wavelength is made steep and sharp to produce strong luminescence, thereby making it possible to obtain a light emitter which has a favorable resolution.

In addition, a method for producing a light-emitter according to the present disclosure comprises preparing the Ag—In precursor solution, preparing the Se precursor solution, the step of preparing the compound semiconductor, and heating the compound semiconductor for the predetermined period of time at the reaction temperature higher than the predetermined temperature for preparing the compound semiconductor, thus improving the crystallinity of the nanoparticles, and thus suppressing the defect generation of the nanoparticles. More specifically, the improved crystallinity reduces the variation in average grain size, and allows for the reduction of the energy loss derived from the defect level, thereby making it possible to obtain, with high efficiency, a light emitter capable of band-edge luminescence with a small half-value width and a small Stokes shift.

The biological substance labelling agent according to the present disclosure is provided with the light emitter described above, thus making it possible to, since the light emitter emits light so as to have a steep and sharp peak wavelength in the near infrared region, dynamically analyze a biological image with a desirable high sensitivity and in multiple colors, and thus obtain a biological substance labeling agent suitable for biomarkers in bioimaging.

DETAILED DESCRIPTION OF EXEMPLARY EMBODIMENTS

Exemplary embodiments of the present disclosure will be described in detail as follows.

Figure 1:
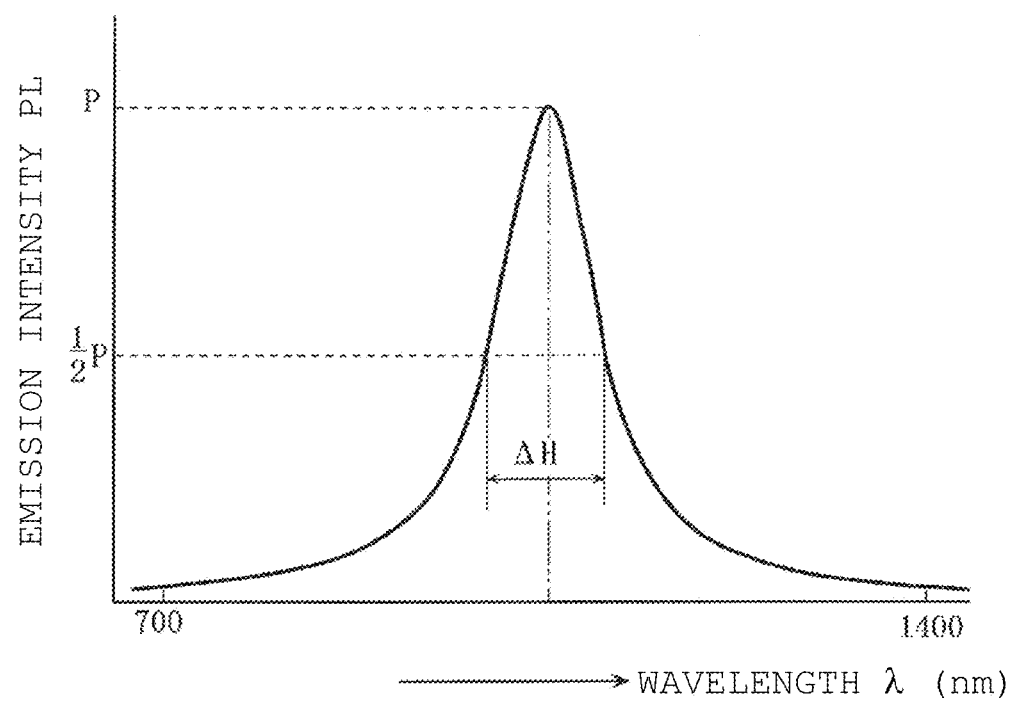
FIG. 1 is a profile showing a main part of an emission spectrum of a light emitter according to an exemplary embodiment.

FIG. 1 is a profile schematically showing a main part of an emission spectrum of a light emitter according to an exemplary embodiment of the present disclosure, where the horizontal axis indicates a wavelength, whereas the vertical axis indicates emission intensity.

The light emitter according to the present disclosure is formed from nanoparticles composed of a compound semiconductor containing an Ag component, an In component, and an Se component (hereinafter, referred to as an "Ag—In—Se based compound semiconductor" for purposes of this disclosure). Further, the peak wavelength of the emission intensity falls within the range of 700 to 1400 nm, and the half-value width $\Delta H$ for the peak wavelength should be 100 nm or less.

Thus, a light emitter is provided that is suitable for a biomarker in bioimaging for confirming a medication effect and a cell state in regenerative medicine, cancer therapy, or the like, thereby making it possible to give fluorescence to a biological substance, and dynamically analyze an image with a high sensitivity and multiple colors.

The reason as to why the peak wavelength of the light emission intensity, the light-emitting material, and the half-value width $\Delta H$ for the peak wavelength are adjusted to fall within the ranges described above will be described below.

(1) Peak Wavelength of Emission Intensity and Light Emitting Material

As described in the Background section above, biological constituent substances, such as hemoglobin, are highly absorbent in the visible light region of shorter than 700 nm, which is shorter in wavelength than the near-infrared region, whereas when the wavelength is longer than 1700 nm, moisture absorption is increased, and for this reason, no light can pass through a living body with high efficiency, and it is difficult to obtain desired biological information even if luminescence is produced in the living body.

On the other hand, the light transmittance with respect to a living body is favorable in the near-infrared region of 700 to 1700 nm in wavelength, which is considered suitable for dynamic image analyses of living tissues through the use of bioimaging technology. In particular, in the near-infrared region, the range of 700 to 1400 nm in wavelength is referred to as a "biological window", which has favorable light transmittance with respect to a living body, and an emission spectrum is obtained such that the emission intensity has a peak wavelength in the foregoing range, thereby making it possible to acquire desired biological information.

Therefore, according to the present disclosure, the peak wavelength of the emission intensity is adjusted to fall within the range of 700 to 1400 nm, preferably 700 to 1000 nm.

Then, an Ag—In—Se based semiconductor compound is used as a light-emitting material that has a peak wavelength in the wavelength range mentioned above.

More specifically, an Ag—In—Se based semiconductor compound that has a chalcopyrite-type crystal structure is low in toxicity unlike a Cd-based material such as CdSe or CdTe, and the composition is adjusted to form a solid solution, thereby allowing the control of the emission wavelength. Moreover, as also described above, the Ag—In—S based semiconductor compound of using S instead of Se, for example, $AgInS_2$ has bandgap energy of 1.87 eV (660 nm in terms of wavelength) in a bulk state, which is large bandgap energy, and produces luminescence in the visible light region, whereas the Ag—In—Se based semiconductor compound, for example, $AgInSe_2$ has bandgap energy of 1.24 eV (1000 nm in terms of wavelength) in a bulk state, which is small bandgap energy, and produces luminescence in the near-infrared region. Therefore, it is believed that the Ag—In—Se based semiconductor compound is made into nanoparticles, and controlled in terms of particle size, thereby exerting a quantum size effect, and even with the same composition, emitting light at various wavelengths in the above-described near-infrared region.

Therefore, according to the present embodiment, an Ag—In—Se based compound semiconductor is used as the light-emitting material.

(2) Half-Value Width ΔH for Peak Wavelength

In order to obtain desired biological information with the use of the bioimaging technique, it is necessary to increase the resolution with strong light emitted by the light emitter, and to that end, there is need for the profile near the peak wavelength of the emission spectrum needs to be steep and sharp. Then, the steepness/sharpness of the peak wavelength can be evaluated by the wavelength width at ½P of the peak wavelength P of the emission intensity, that is, the half-value width ΔH.

The half-value width ΔH is related to the Stokes shift S, and hereinafter, the relationship between the Stokes shift S and the half-value width ΔH will be described.

Figure 2:
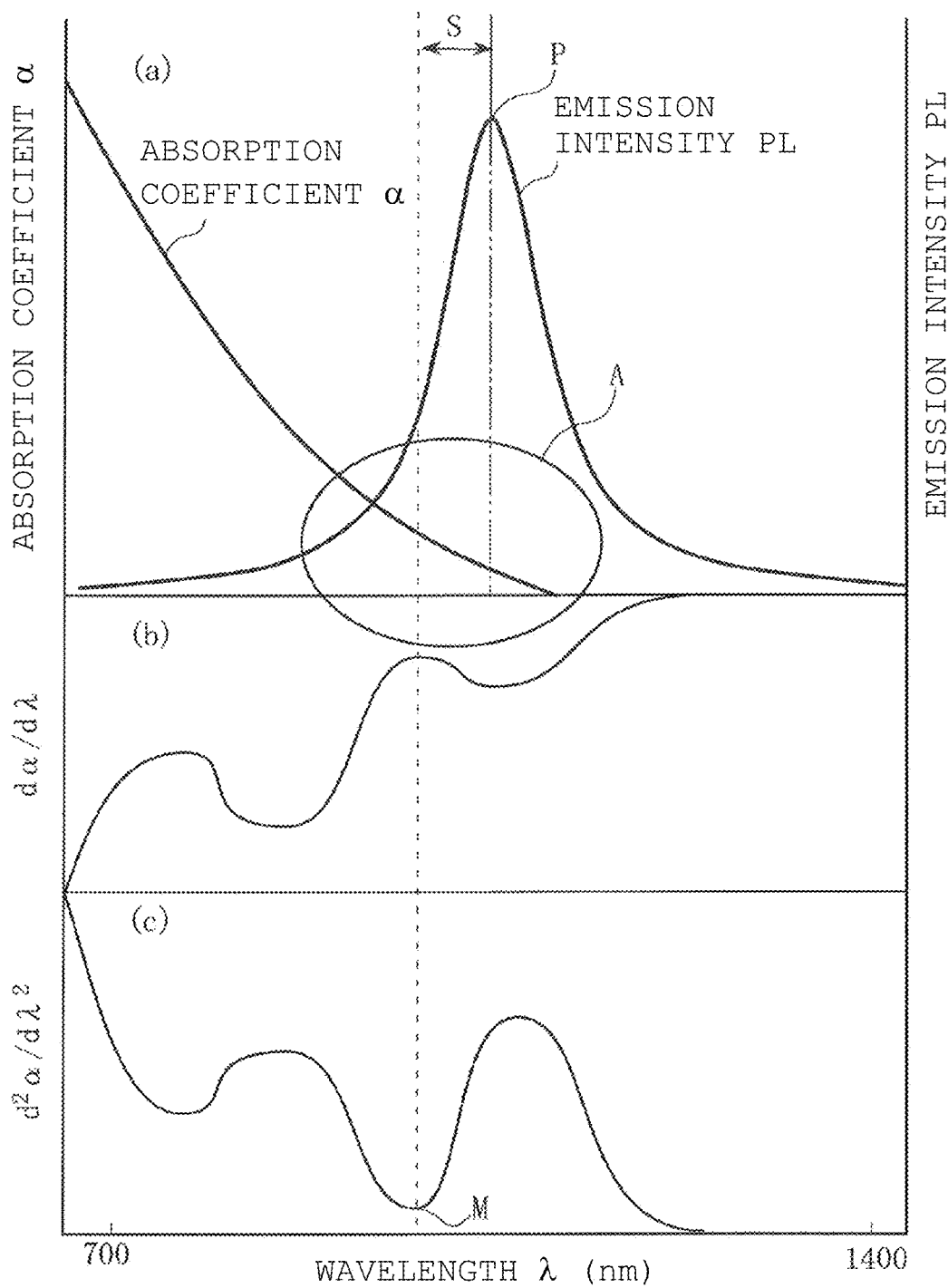
FIG. 2 is a profile showing an example of an emission spectrum, an absorption spectrum, and a Stokes shift of a light emitter according to an exemplary embodiment.

FIG. 2 is a profile showing the relationship among an absorption spectrum, an emission spectrum, and a Stokes shift S.

As shown in section (a) of FIG. 2, a profile with the absorption spectrum and the emission spectrum, where the horizontal axis indicates a wavelength λ, the left vertical axis indicates an absorption coefficient α, and the right vertical axis indicates an emission intensity PL.

As shown in section (b) of FIG. 2, a profile of a derivative $d\alpha/d\lambda$ for differentiating the absorption coefficient α once with the wavelength λ, where the horizontal axis indicates a wavelength λ, whereas the vertical axis indicates $d\alpha/d\lambda$.

As shown in section (c) of FIG. 2, a profile of a second order derivative $d^2\alpha/d\lambda^2$ for differentiating the absorption coefficient α twice with the wavelength λ, where the horizontal axis indicates a wavelength λ, whereas the vertical axis indicates $d^2\alpha/d\lambda^2$.

When photon energy is imparted to the light emitter, the light absorber absorbs light, thereby exciting electrons in the valence band in the ground state to the conduction band, and forming holes in the valence band. Then, the excited electrons are attracted to the valence band side in the ground state where holes are present due to the Coulomb force, and the electrons and the holes are recombined to produce luminescence. In this case, when the photon energy is partially consumed for vibration energy and the like by electrons returning from the excited state to the valence band side, a deviation referred to as a Stokes shift S is produced between the absorption wavelength and the emission wavelength.

On the other hand, if the crystal structures of the nanoparticles have defects, the defects forms various energy levels, that is, defect levels between bands. Therefore, when electrons excited by light absorption transit from the conduction band to the valence band, the electrons are believed to transition through a relaxation process by the defect levels mentioned above. More specifically, the excited electrons are accompanied by energy loss, and recombined with holes at the above-mentioned defect levels to produce luminescence (defect luminescence). Further, the defects can take various levels between the bands as described above, the energy consumed by the transition from the conduction band to the valence band will thus also vary, and for this reason, the defect luminescence will have an emission spectrum with a large half-value width αH, which reflects the energy loss. Therefore, in order to obtain a light emission with a small half-value width αH and a steep and sharp peak wavelength, it is necessary to suppress defect luminescence, and to that end, it is necessary to reduce the energy loss due to defects, photon vibrations, and the like. Further, since this energy loss produces a Stokes shift S that indicates a deviation between the absorption wavelength and the emission wavelength, the reduction in Stokes shift S can narrow the half-value width αH, thereby allowing the emission characteristics to be improved.

Therefore, according to the present embodiment, through the reduction in Stokes shift S, the half-value width αH for the peak wavelength is adjusted to 100 nm or less as described above, thereby a high-resolution light emitter suitable for a biomarker with energy loss suppressed.

This Stokes shift S is, as shown in FIG. 2, quantitatively evaluated by the difference between the minimum value M of the second order derivative $d^2\alpha/d\lambda^2$ which is the change rate of the tangent of the absorption coefficient α and the peak wavelength P of the emission wavelength.

In order to make the half-value width αH 100 nm or less, experimentally, the Stokes shift S is desirably 180 nm or less, preferably 70 nm or less, although it is difficult to evaluate the Stokes shift S theoretically.

In addition, when the emission wavelength is 700 to 1400 nm which corresponds to the biological window, the emission wavelength is brought close to the absorption wavelength, with a small Stokes shift S, as long as a falling skirt part A of the absorption wavelength falls within the wavelength range of 700 to 1000 nm in the absorption spectrum. Therefore, both the light absorption process and the light emission process are enabled in the wavelength range of 700 to 1400 nm, and excited luminescence can be thus achieved effectively through the use of the biological window.

As long as the Stokes shift S is extremely small as just above, the band-edge luminescence with high energy efficiency with energy loss suppressed is obtained, thereby making it possible to achieve both an efficient emission and a steep and sharp peak wavelength.

It is to be noted that when the half-value width $\alpha H$ for the peak wavelength exceeds 100 nm, the peak wavelength is excessively broadened, and the peak wavelength draws a shallow curve without steepness and with the lack of sharpness, thus leading to a decrease in resolution, and making it difficult to obtain a lot of biological information in the range of 700 to 1400 nm. In addition, there is unfavorably a possibility that the wavelength range of the emission intensity may be partially less than 700 nm, or may greater than 1400 nm.

In addition, the composition ratios of the respective components of the Ag—In—Se based compound semiconductor are not to be considered particularly limited as long as the peak wavelength of the emission intensity is 700 to 1400 nm, and as long as the half-value width $\alpha H$ for the peak wavelength is 100 nm or less, but it is preferable to contain the In component in excess of the stoichiometric composition.

While the stoichiometric compositions of the Ag component and the In component meet 1:1, containing the In component for production in excess of the stoichiometric composition is believed to make it possible to suppress the non-radiative deactivation process of emitting no light when excited electrons return to the ground state, thereby allowing for obtaining an emission peak with intensity further improved. However, when containing the In component for production in excess of the stoichiometric composition, there is possibility that impurities such as different phases may be produced, and for this reason, there is also a possibility that a decrease in purity may be caused, thereby rather decreasing the intensity of the emission peak. In consideration of the foregoing, in the case of containing the In component for production in excess of the stoichiometric composition, the combination ratio of the In component to the Ag component is preferably from 1.5 to 3 in terms of molar ratio.

In addition, the average particle size of the Ag—In—Se based compound semiconductor is not to be considered particularly limited as long as a quantum size effect is exhibited in the wavelength region of 700 to 1400 nm, and for example, nanoparticles in the range of 0.1 to 20 nm can be used.

It is to be noted that as long as the exemplary embodiments of the present disclosure are adapted to satisfy the three requirements: (i) it is formed from nanoparticles composed of a compound semiconductor containing an Ag component, an In component, and an Se component; (ii) the peak wavelength of emission intensity falls within the range of 700 nm to 1400 nm; and (iii) the half-value width $\alpha H$ for the peak wavelength is 100 nm or less, the production method is not to be considered particularly limited.

Next, an embodiment of a method for producing the light emitter will be described in detail.

First, an Ag compound containing an Ag component and an In compound containing an In component are prepared, and the Ag compound and the In compound are each weighed such that the combination ratio between the Ag component and the In component after synthesis preferably makes the In component in excess of the stoichiometric composition. The In component is combined in excess of the stoichiometric composition, thereby causing the absorption wavelength to shift to the longer wavelength side, thus making it to bring the absorption wavelength close to the emission wavelength, and allowing band-edge luminescence.

However, when the composition ratio of the In component to the Ag component is excessively increased, impurities such as different phases are estimated to be produced, and thus, the Ag compound and the In compound are preferably weighed such that the element ratio (In/Ag) is 1.5 to 3 in terms of molar ratio.

It is to be noted that the types the compounds used for the Ag compound and the In compound are not to be considered particularly limited, but metal complexes that are relatively inexpensive, chemically stable, and easily available, for example, $Ag(OCOCH_3)$ (silver acetate) and $In(OCOCH_3)_3$ (indium acetate) can be preferably used which have, as a ligand, a carboxylate ion such as an acetate ion.

Next, these weighed materials are dissolved in a high boiling point solvent to prepare an Ag—In precursor solution. The high boiling point solvent is not to be considered particularly limited as long as the solvent is high in boiling point and chemically stable at high temperature, and a mixed solution can be used which includes, for example, at least one selected from 1-dodecanethiol, octadecene, oleylamine, and n-octyl ether.

In addition, a Se powder is prepared, and this Se powder is dissolved in a solvent to prepare a Se precursor solution. The solvent is not to be considered particularly limited, and for example, a mixed solution of an alkylthiol such as 1-dodecanethiol and hexanethiol and an alkylamine such as oleylamine, and a phosphine such as tributylphosphine and trioctylphosphine can be used.

Then, the Ag—In precursor solution is put in a container, degassed under reduced pressure, and then purged with nitrogen. Thereafter, a heat treatment is carried out to raise the temperature of the reaction field from room temperature to a predetermined temperature (for example, 150° C.)

Next, the Se precursor solution is injected into the Ag—In precursor solution heated to the predetermined temperature, then heated to a predetermined reaction temperature, and kept at the reaction temperature for a predetermined period of reaction time, thereby providing a reaction product.

In this regard, the reaction temperature is preferably higher than the predetermined temperature, for example, 200° C. or higher, thereby making it possible to promote grain growth moderately to such an extent that the nanoparticles are not coarsened. As a result, the nanoparticles have crystallinity improved with defect generation suppressed, and also have a reduced variation in average particle size, thereby reducing the Stokes shift S, and thus making it possible to obtain a peak wavelength with a small in half-value width $\Delta H$.

In addition, the reaction time is not to be considered particularly limited, and can be set to be, for example, 30 to 120 minutes. Further, grain growth can be controlled by varying the reaction time, and the average grain size can be thus adjusted. Yet further, the adjustment of the average grain size varies the emission wavelength due to the quantum size effect, and the peak wavelength of the emission intensity can be thus controlled.

Next, this reaction product is left to cool until reaching room temperature, and then centrifuged to separate into a supernatant liquid and a precipitate, and the supernatant liquid is collected, and the precipitate is discarded. Then, a poor solvent such as methanol, ethanol, acetone, or acetonitrile is added to the supernatant liquid to form a precipitate, and the precipitate is separated and collected by centrifugation again. Subsequently, the operation of: the addition of the poor solvent→centrifugation treatment→the collection of the precipitate is repeated more than once to prepare a high-purity precipitate containing no impurities such as different phases. Then, this precipitate is dissolved through the addition of a nonpolar solvent such as chloroform, toluene, or hexane, thereby making it possible to prepare a dispersion solution of Ag—In—Se based compound semiconductor nanoparticles dispersed therein.

As described above, a method for producing a compound semiconductor according to an exemplary embodiment of the present disclosure includes preparing an Ag—In precursor solution by dissolving an Ag compound and an In compound in a high boiling point solvent, dissolving the Se powder in a solvent to prepare a Se precursor; injecting the Se precursor solution into the Ag—In precursor solution while heating the Ag—In precursor solution to a predetermined temperature to prepare a mixed solution; and heating the reaction temperature at a reaction temperature higher than the predetermined temperature for a predetermined reaction time, so that the crystallinity of the nanoparticles is improved and defect formation of the nanoparticles is suppressed. More specifically, the improved crystallinity reduces the variation in average grain size, and allows for the reduction of the energy loss derived from the defect level, thereby making it possible to obtain, with high efficiency, a light emitter capable of band-edge luminescence with a small half-value width αH and a small Stokes shift.

Further, the biological substance labelling agent is provided with the present light emitter, thereby making it possible to, since the light emitter emits light so as to have a steep and sharp peak wavelength in the near infrared region, dynamically analyze a biological image with a desirable high sensitivity and multiple colors. As such, a biological substance labeling agent is provided that is suitable for biomarkers in bioimaging.

It is to be noted that the present invention is not to be considered limited to the embodiment mentioned above. The above-mentioned embodiment is an exemplary embodiment of the present invention, which can be obviously changed unless the spirit is changed.

In addition, the light emitter according to the exemplary embodiment can be used as a biological substance labeling agent as described above, and also utilized for a light source for exciting a label in a living organism. For example, when a sealed part of a blue light emitting diode or an ultraviolet light emitting diode is filled with the nanoparticles according to the present disclosure, the nanoparticles are excited by the blue light emitting diode or the ultraviolet light emitting diode to emit light in the near-infrared region of 700 to 1400 nm, which can be used as light for exciting a label in a living body in the foregoing wavelength range.

Next, examples of the present invention will be specifically described.

EXAMPLE 1

[Preparation of Sample]

Prepared were: Ag(OCOCH$_3$) with a purity of 99% (manufactured by Nacalai Tesque, Inc.) and In(OCOCH$_3$)$_3$ with a purity of 99.99% (trade name "Alfa Aesar", manufactured by Johnson Matthey Catalyst); a selenium powder with a purity of 99.99% (manufactured by Kojundo Chemical Laboratory Co., Ltd.); 1-octadecene with a purity of 90% (manufactured by Sigma-Aldrich); and 1-dodecanethiol (manufactured by Tokyo Chemical Industry Co., Ltd.), and an oleylamine with a purity of 80 to 90% (manufactured by Across Organics Inc.) as a solvent.

Then, the Ag(OCOCH$_3$) and the In(OCOCH$_3$)$_3$ were weighed for 0.2 mmol of in total so that the Ag/In ratio after synthesis was 1/1 to 1/8.

Next, this weighed material was put into a three-necked flask with an internal volume of 50 mL together with a stirrer chip, and then, 8 mL of the octadecene and 1 mL of the 1-dodecanethiol were added thereto as a high boiling point solvent, and stirred to prepare an Ag—In precursor solution.

In addition, 0.2 mmol of the Se powder was dissolved in 1 mL of 1-dodecanethiol and 1 mL of oleylamine as a solvent to prepare a Se precursor solution.

Next, the interior of the three-necked flask with the Ag—In precursor solution accumulated therein was degassed under reduced pressure, and then purged with nitrogen, and thereafter, the three-necked flask was heated with a heater to raise the temperature the temperature from room temperature. Then, with the temperature of the reaction field at 150° C., the Se precursor solution was injected into the three-necked flask, the temperature of the reaction field was raised up to 200° C., and at this temperature, a heat treatment was carried out for 30 minutes, thereby providing a reaction product.

Next, this reaction product was air-cooled to room temperature, and then centrifuged at 5000 rpm for 5 minutes to separate into a supernatant liquid and a precipitate, and the supernatant liquid was collected, and the precipitate was discarded.

Next, methanol (poor solvent) that was about 3 times as large as the volume of the supernatant liquid was added to precipitate crystal particles. Thereafter, the crystal particles were collected by centrifugation again, 3 mL of methanol was added to the collected precipitate, and the crystal particles were collected again by centrifugation. Thereafter, the operation of: the addition of methanol→centrifugation→the collection of crystal particles was repeated more than once, and the obtained high-purity crystal particles were dispersed in chloroform as a nonpolar solvent, thereby preparing samples of sample numbers 1 to 6.

[Evaluation of Sample]

The absorption spectrum, the emission spectrum, the half-value width for the peak wavelength, the Stokes shift S, and the absolute emission quantum yield (hereinafter referred to simply as a "quantum yield") were determined for each of the sample numbers 1 to 6.

Specifically, the emission spectrum and the quantum yield were measured at room temperature of 25° C. with the use of an absolute emission quantum yield measurement device (C9920-02, manufactured by Hamamatsu Photonics K.K.), and the full width at half maximum for the peak wavelength was determined from the emission spectrum.

In addition, the absorption spectrum was measured at room temperature of 25° C. with the use of a spectrophotometer (U4100 manufactured by Hitachi High-Technologies Corporation).

In addition, the Stokes shift S was calculated on the basis of the peak wavelength of the emission intensity PL of the sample and the absorption coefficient α.

Figure 3:
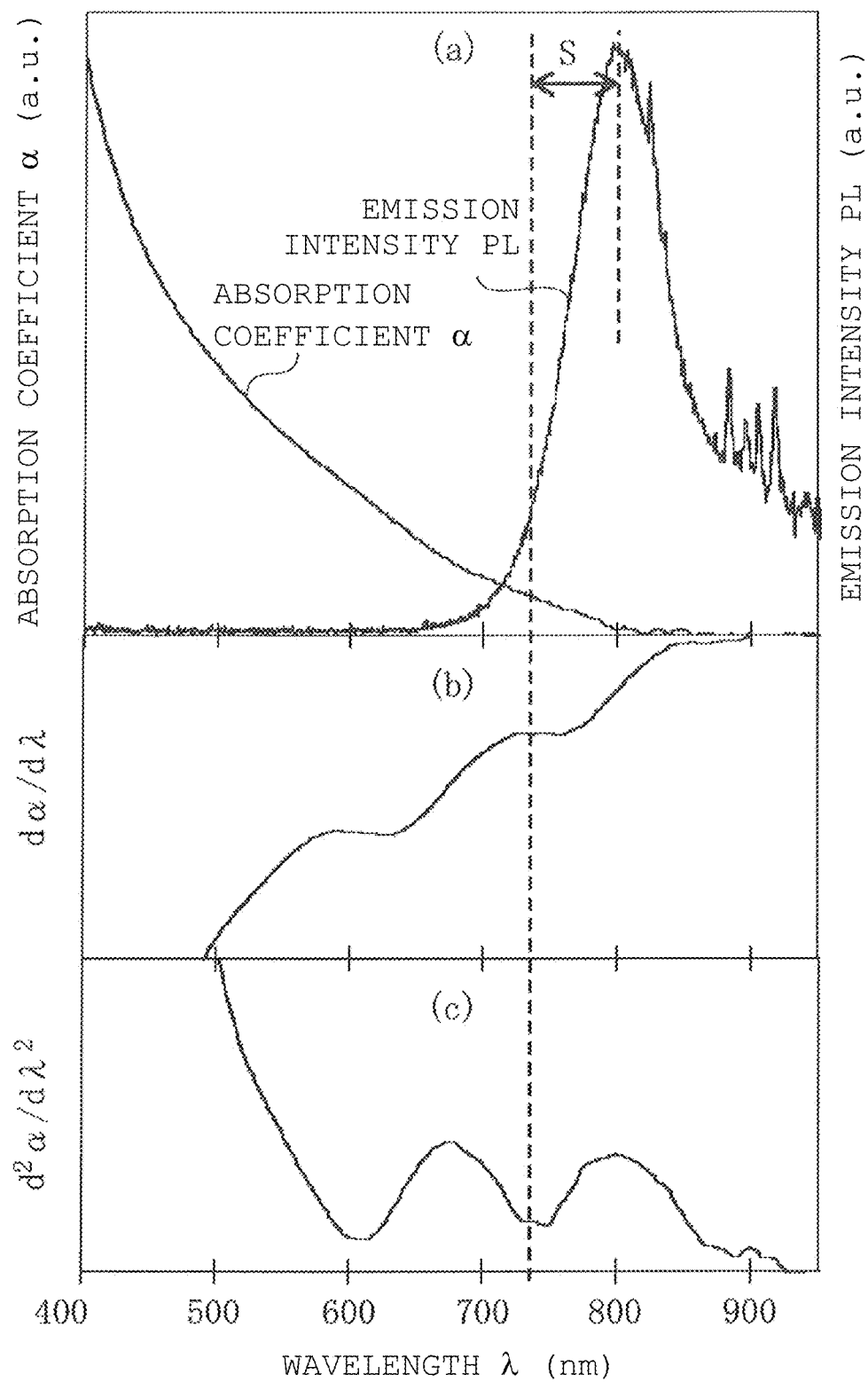
FIG. 3 is a profile diagram of an emission spectrum, an absorption spectrum, and a Stokes shift for sample number 3 according to Example 1.

FIG. 3 is a diagram showing the relationship among the emission spectrum, the absorption spectrum, and the Stokes shift for sample number 3.

As shown in section (a) of FIG. 3, the emission spectrum and the absorption spectrum for sample number 3, where the horizontal axis indicates a wavelength λ (nm), the left vertical axis indicates an absorption coefficient α (a.u.), and the right vertical axis indicates an emission intensity PL (a.u.).

As shown in section (b) of FIG. 3, a profile diagram of a derivative for differentiating the absorption coefficient α for sample number 3 once with the wavelength λ, where the horizontal axis indicates a wavelength λ (nm), whereas the vertical axis indicates a derivative dα/dλ.

As shown in section (c) of FIG. 3, a profile diagram of a second order derivative for differentiating the absorption coefficient α for sample number 3 twice with the wavelength λ, where the horizontal axis indicates a wavelength λ (nm), whereas the vertical axis indicates a second order derivative $d^2\alpha/d\lambda^2$.

Then, the difference between the peak wavelength of the emission intensity and the wavelength for the minimum of the second order derivative $d^2\alpha/d\lambda^2$ was calculated, and regarded as the Stokes shift S. More specifically, the Stokes shift S can be calculated on the basis of the peak wavelength of the emission intensity PL of the sample and the absorption coefficient α.

Although not shown in the figure, Stokes shift S was also calculated in the same manner for sample numbers 2, 4, and 5.

Figure 4:
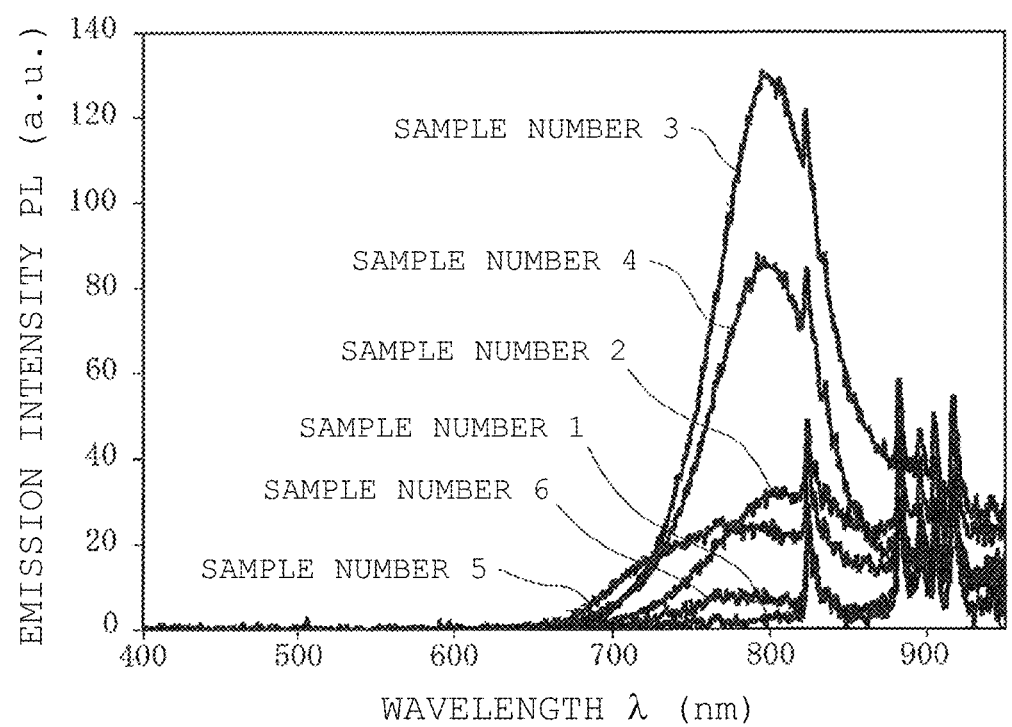
FIG. 4 is a profile showing emission spectra for each sample according to Example 1.

FIG. 4 shows the emission spectra for sample numbers 1 to 6, where the horizontal axis indicates a wavelength λ (nm), whereas the vertical axis indicates an emission intensity PL (a.u.).

In addition, Table 1 shows the Ag/In ratio, the half-value width, the Stokes shift, and the quantum yield for sample numbers 1 to 6.

TABLE 1

| Sample No. | Ag/In Ratio | Half-Value Width (nm) | Stokes shift (nm) | Quantum Yield (%) |
|---|---|---|---|---|
| 1 | 1/1 | <100 | — | 1.1 |
| 2 | 1/1.5 | <100 | 72 | 5.1 |
| 3 | 1/2 | 85 | 65 | 12 |
| 4 | 1/3 | 82 | 175 | 7.7 |
| 5* | 1/4 | 167 | 170 | 4.1 |
| 6 | 1/8 | <100 | — | 1.5 |

*outside the scope of the present disclosure.

As clearly shown in FIG. 4, it is determined that sample numbers 1 to 6 all emit light in the near-infrared region of 700 to 1000 nm, which is referred to as a "biological window" for purposes of this disclosure.

However, Sample No. 5 has failed to achieve a steep peak waveform, since the half-value width was as wide as 167 nm. This is believed to be, even with In in excessive of the stoichiometric composition, impurities such as different phase were mixed in the sample.

On the other hand, it has been determined that sample numbers 1 to 4 and 6 achieve peak wavelengths of 100 nm or less in half-value width in the wavelength region of 700 to 1000 nm.

It is to be noted that sample numbers 1 and 6 are as low in quantum yield as 1.1 to 1.5%, and thus inferior in emission intensity, but 100 nm or less in half-value width in the wavelength region of 700 to 1000 nm, and thus, the matters specified in the present disclosure are satisfied, while the emission intensity is low.

From the foregoing, it has been determined that the appropriate control of the Ag/In ratio achieves a light emitter which has favorable emission characteristics with a half-value width of 100 nm or less in the wavelength region of 700 to 1000 nm, referred to as a "biological window" for purposes of this disclosure.

In addition, it has been determined that sample numbers 2 to 4 of 100 nm or less in half-value width, are also 65 nm to 175 nm in Stokes shift, which is 180 nm or less, thereby making it possible to achieve light emitters with reduced energy loss derived from the defect levels.

Figure 5:
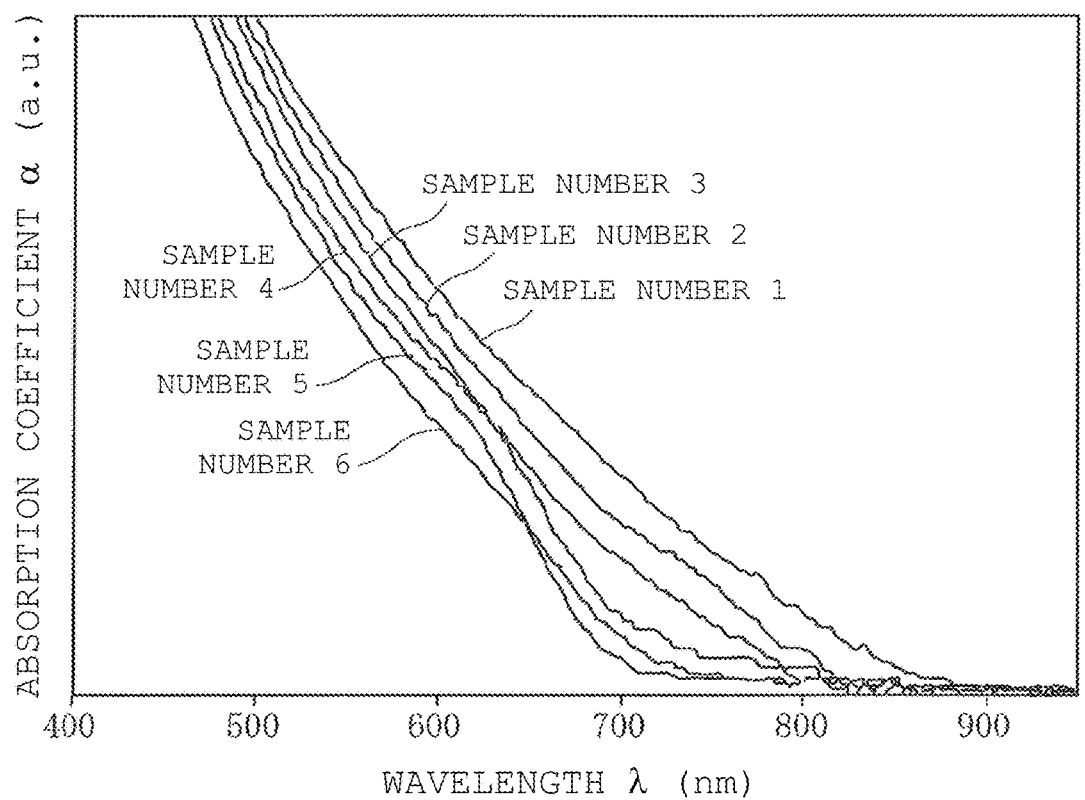
FIG. 5 is a profile of enlarged falling skirt parts of absorption spectra for each sample according to Example 1.

FIG. 5 is a diagram showing the falling skirt part of the absorption spectrum, where the horizontal axis indicates a wavelength λ (nm), whereas the vertical axis indicates an absorption coefficient α (a.u.).

As is clear from FIG. 5, as the Ag/In ratio is lower, that is, as the sample is richer in In, the absorption wavelength is shifted to the shorter wavelength side, and thus, it has been determined that the Ag/In ratio is adjusted, thereby making it possible to adjust the absorption edge wavelength.

In addition, as is clear from FIG. 5, the falling skirt part of the absorption spectrum is shorter than the wavelength (=1000 nm) of the bulk $AgInSe_2$, and thus, it has been determined that ultrafine atomization shortens the absorption wavelength to increase the bandgap energy, thereby producing a quantum size effect due to the variation in the average grain size.

EXAMPLE 2

A sample according to sample number 11 was prepared by the same method and procedure as for sample number 3 according to Example 1 except that the reaction time was adjusted to 120 minutes.

Next, for the sample of sample number 11, an emission spectrum and a quantum yield were determined by the same method and procedure as in Example 1, and the peak wavelength and the half-value width were determined from the emission spectrum.

Figure 6:
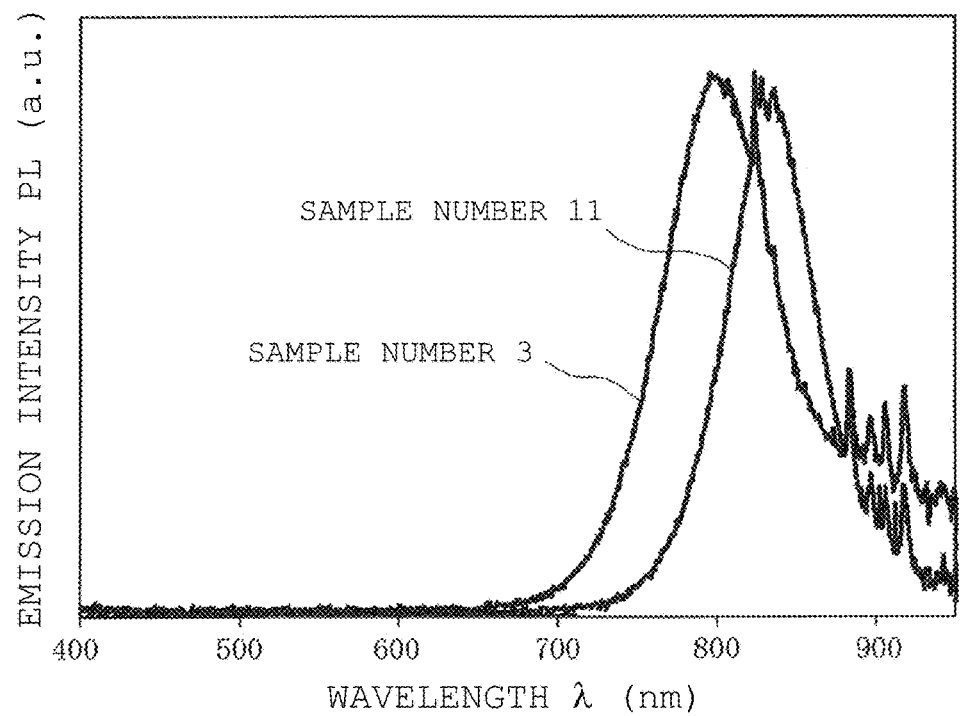
FIG. 6 is a profile showing emission spectra for sample number 3 and sample number 11 according to Example 2.

FIG. 6 is a diagram showing the emission spectrum of sample number 11 together with the emission spectrum of sample number 3, where the horizontal axis indicates a wavelength λ (nm), whereas the vertical axis indicates an emission intensity PL (a.u.).

Sample number 11 was 85 nm in half-value width, and 12% in quantum yield as is the case with sample number 3, but as shown in FIG. 6, the peak wavelength was substantially parallel shifted to the longer wavelength side with respect to sample number 3, and the peak wavelength was about 850 nm. This is believed to be due to the fact that the reaction time was 120 minutes for heating for a longer period of time as compared with sample number 3 for which the reaction time was 30 minutes, thus promoting grain growth, increasing the average grain size, and making a shift to the longer wavelength side.

It has been determined that the adjustment of the reaction time according to the present example as just described can control the average grain size, thereby allowing for the control of the peak wavelength of the emission intensity.

Next, an X-ray diffraction spectrum was measured with the use of an X-ray diffractometer (RINT-K1, manufactured by Rigaku Corporation).

Figure 7:
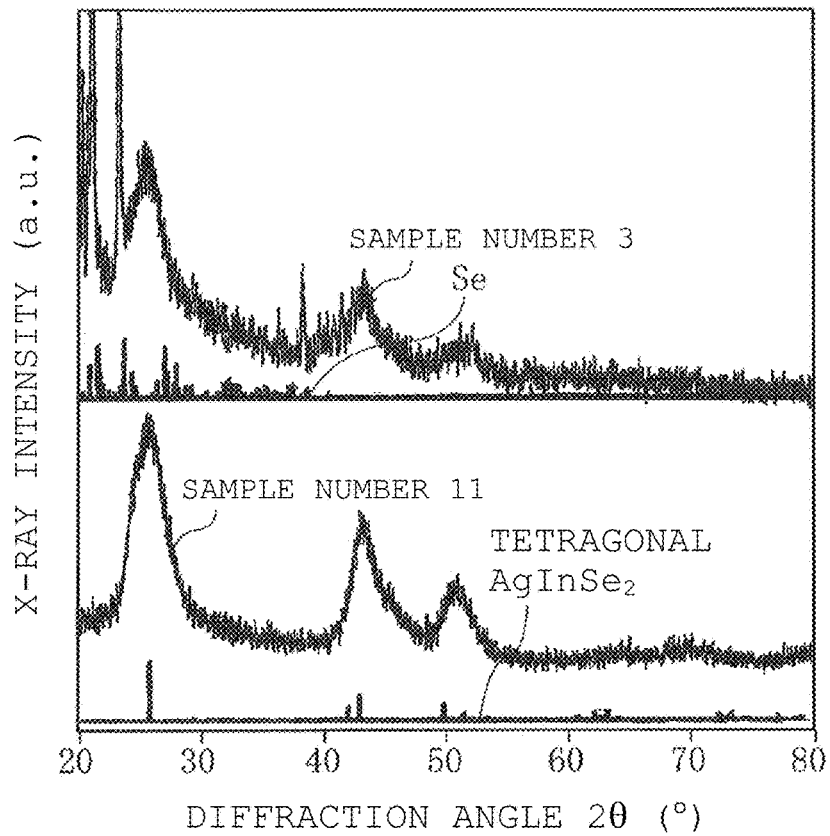
FIG. 7 is a diagram showing X-ray diffraction spectra for sample number 3 and sample number 11, together with diffraction profiles of Se and tetragonal $AgInSe_2$ as standard samples.

FIG. 7 shows the X-ray diffraction spectra for sample number 3 and sample number 11 together with diffraction patterns of Se and tetragonal $AgInSe_2$, wherein the horizontal axis indicates a diffraction angle 2θ (°) and the vertical axis indicates an X-ray intensity (a.u.).

Both sample number 3 and sample number 11 substantially coincided with the diffraction pattern of tetragonal AgInSe$_2$, and it has been confirmed that the Ag—In—Se based compound has semiconductor nanoparticles obtained.

However, a peak wavelength derived from Se was detected in the case of sample number 3 for which the reaction time was 30 minutes.

On the other hand, a peak wavelength derived from Se was not detected in the case of sample number 11 for which the reaction time was 120 minutes. This is believed to be due to the fact that crystallinity is improved by making the reaction time longer, thereby providing a high-purity Ag—In—Se based compound semiconductor.

EXAMPLE 3

Samples of sample numbers 21 to 23 were prepared by the same method and procedure as for sample number 3 according to Example 1, except that oleylamine was used as a high boiling point solvent instead of octadecene, the reaction time was adjusted to 120 minutes, and the reaction time was adjusted to 150° C., 200° C., and 250° C.

For each sample of numbers 21 to 23, emission spectra were measured by the same method and procedure as in Example 1, and the peak wavelength and the half-value width were determined from the emission spectra.

Figure 8:
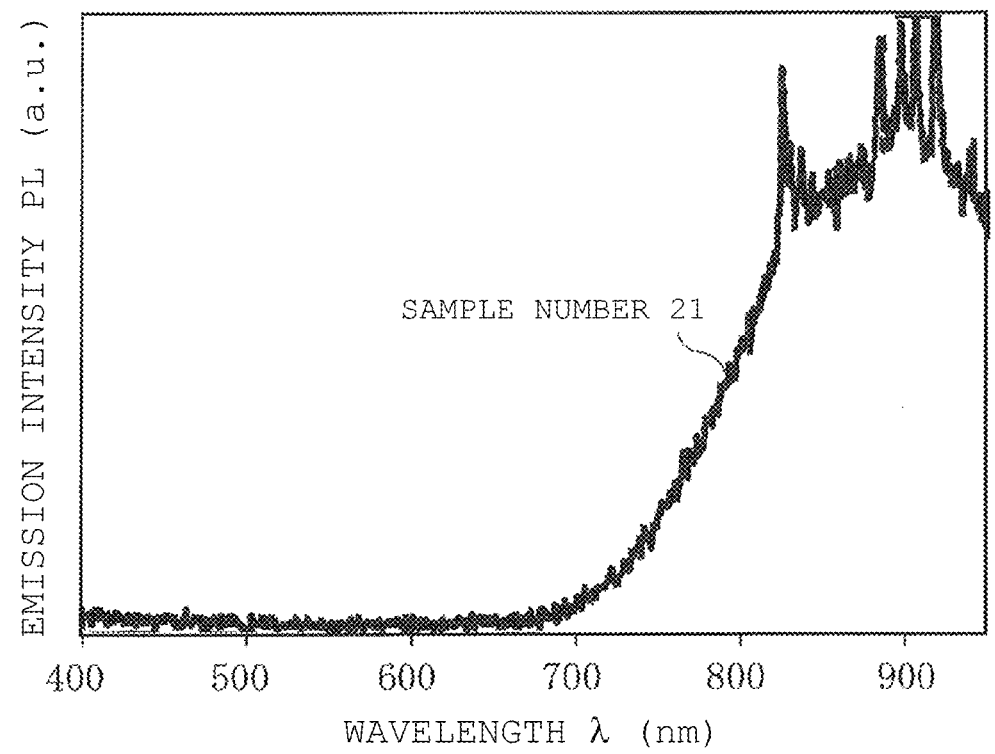
FIG. 8 is a profile showing an emission spectrum for sample number 21 according to Example 3.
Figure 9:
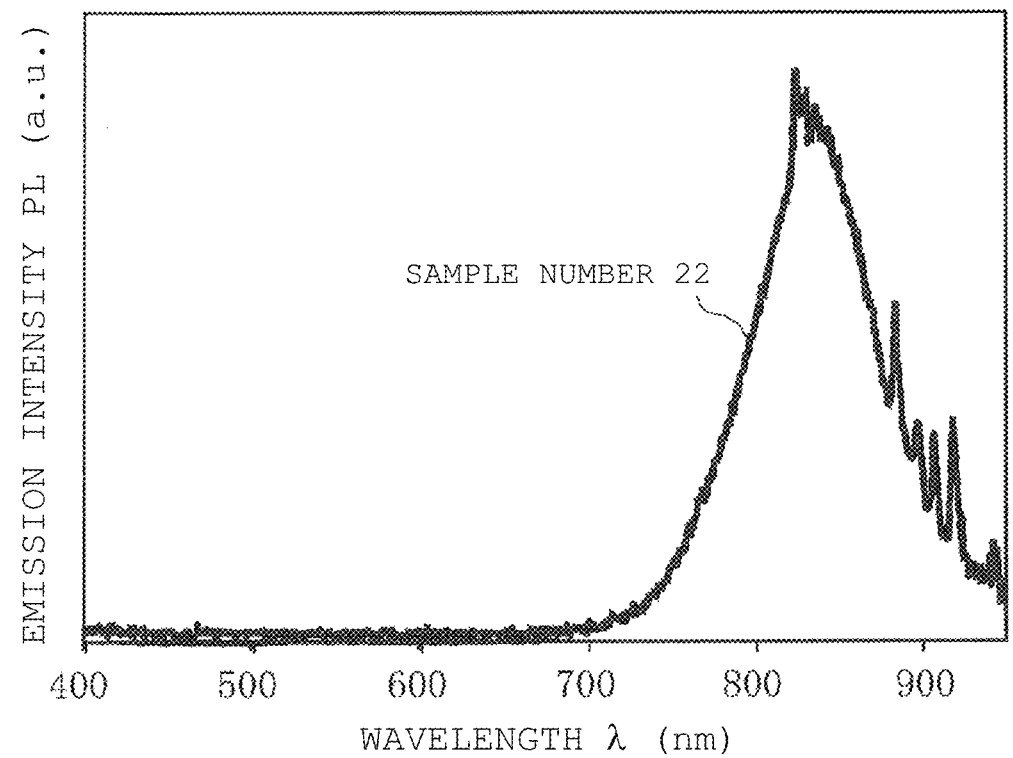
FIG. 9 is a profile showing an emission spectrum for sample number 22 according to Example 3.
Figure 10:
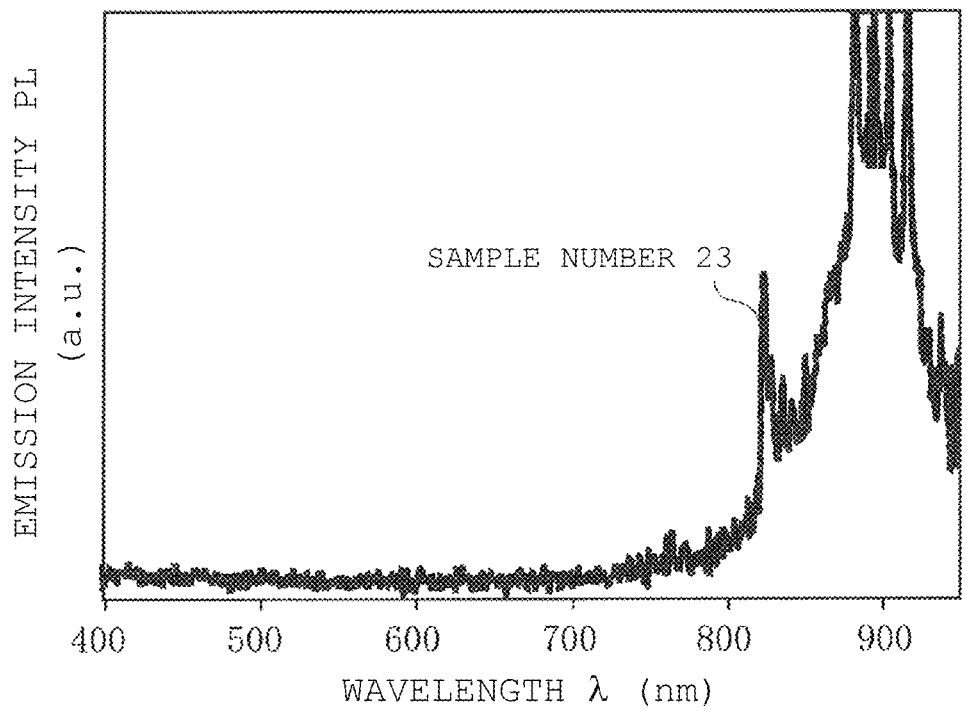
FIG. 10 is a profile showing an emission spectrum for sample number 23 according to Example 3.

FIGS. 8 to 10 illustrate the respective emission spectra of sample numbers 21 to 23, where the horizontal axis indicates a wavelength λ (nm), whereas the vertical axis indicates an emission intensity PL (a.u.).

In addition, for each sample of sample numbers 21 to 23, STEM images were taken at 600,000-fold magnification with the use of a scanning transmission electron microscope (HD-2300A, manufactured by Hitachi High-Technologies Corporation).

Figure 11:
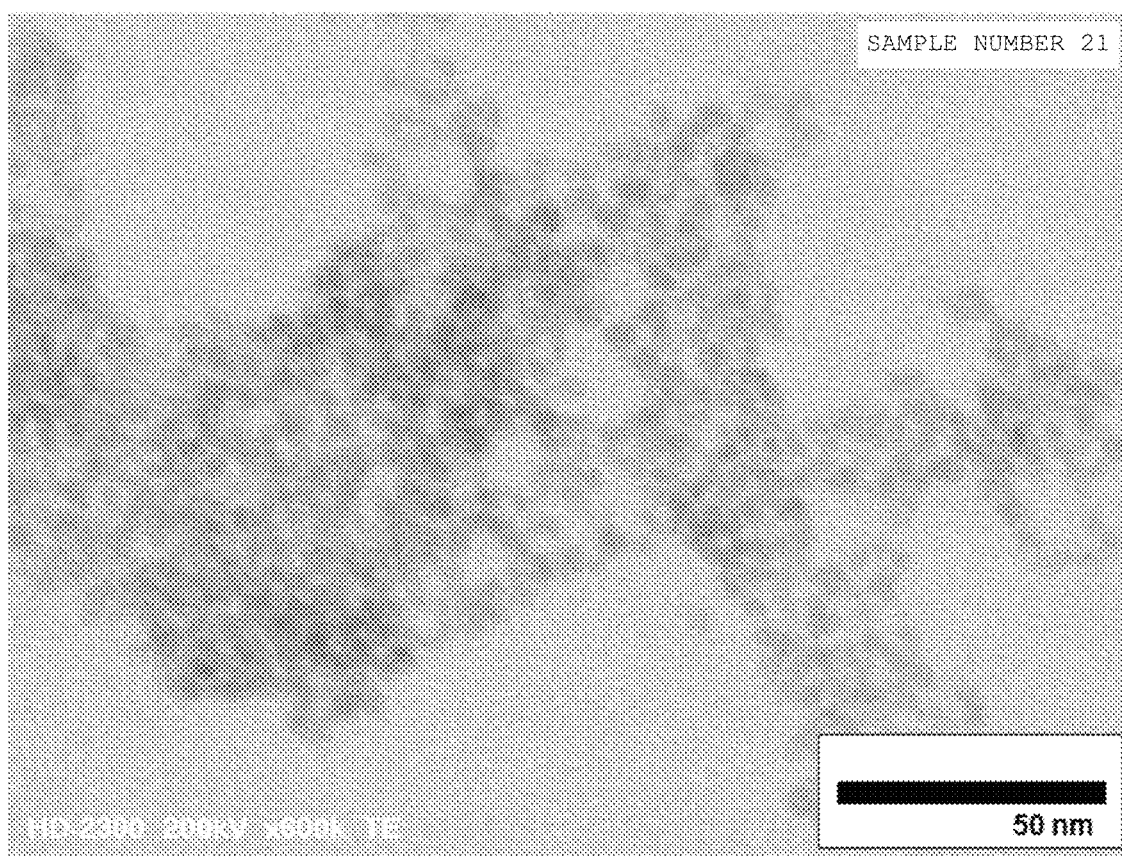
FIG. 11 is a TEM image for sample number 21 mentioned above.
Figure 12:
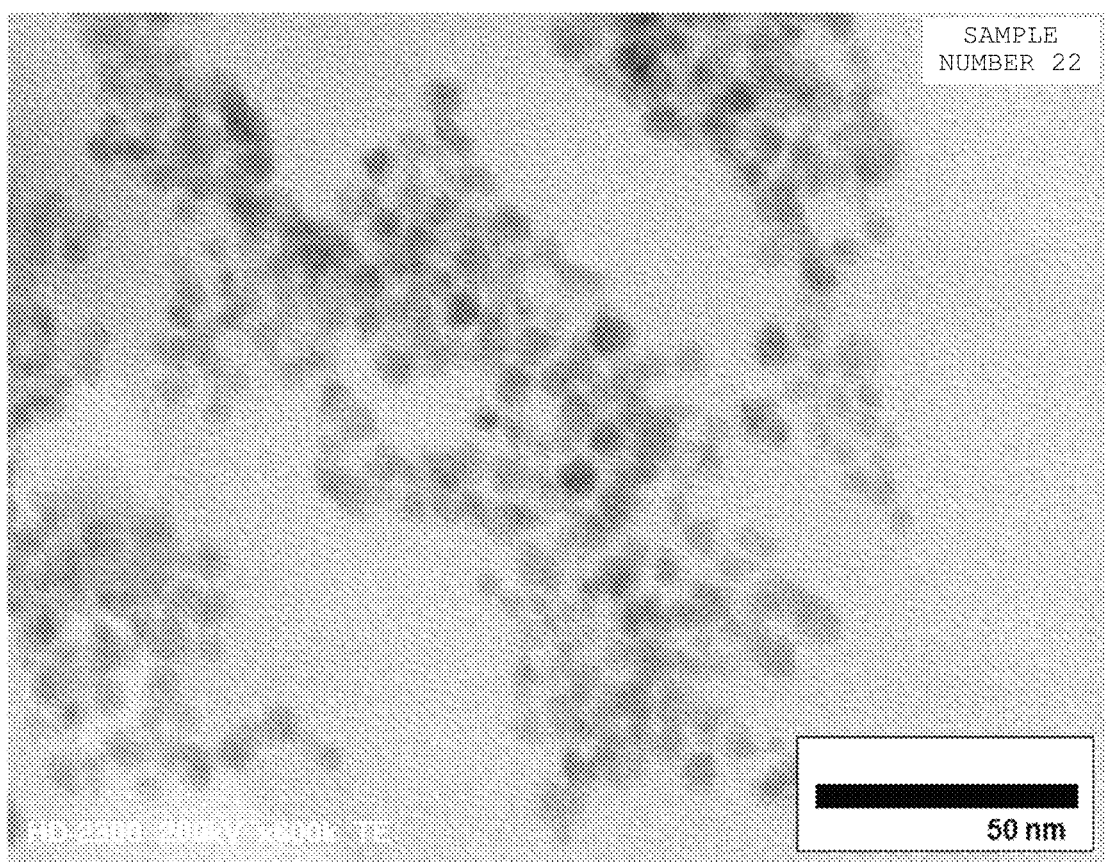
FIG. 12 is a TEM image for sample number 22 mentioned above.
Figure 13:
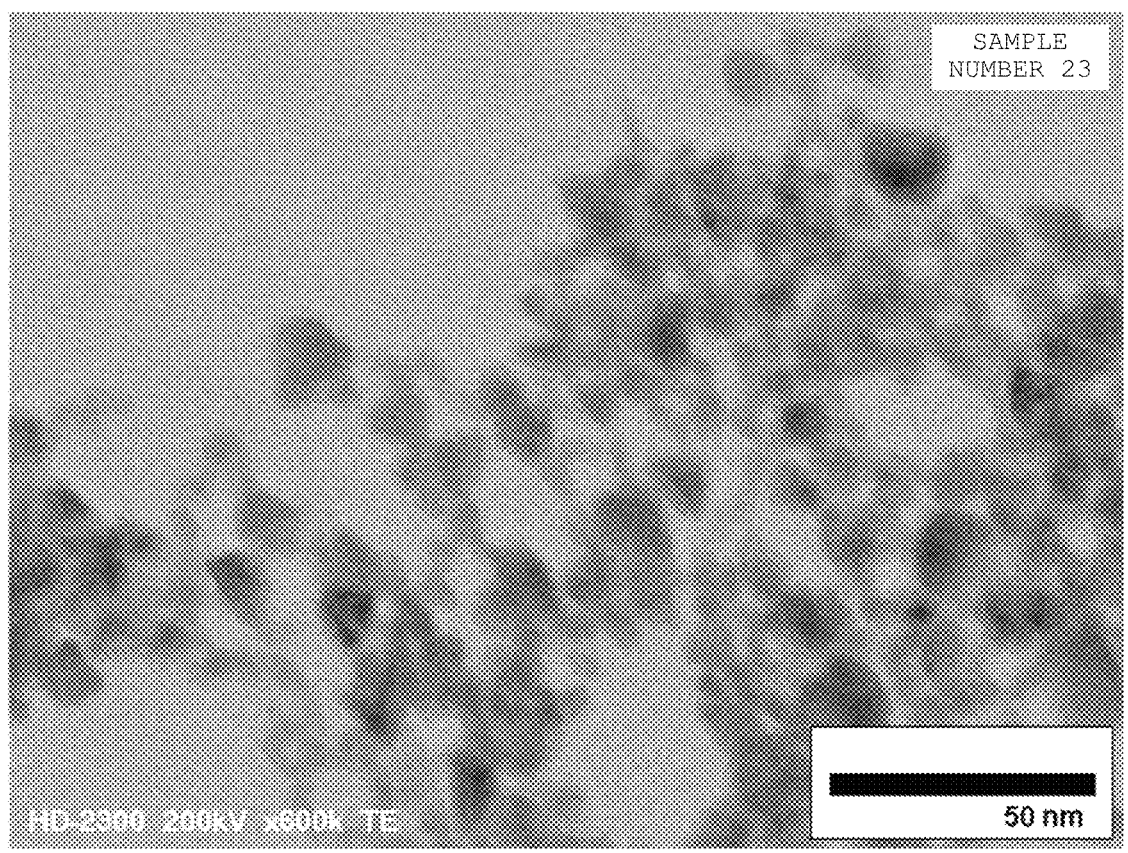
FIG. 13 is a TEM image for sample number 23 mentioned above.

FIGS. 11 to 13 illustrate the respective STEM images of sample numbers 21 to 23.

From the areas for field of view, observed in the STEM images as shown in FIGS. 11 to 13, 100 crystal grains were randomly extracted, and the maximum aspect diameter (Krummbein diameter) was measured for each crystal grain. Then, for each crystal grain, the average value for the measured values was regarded as an average grain diameter Dav, and the standard deviation σ was determined.

Table 2 shows the average grain diameters Dav, standard deviations σ, emission spectra, and STEM image numbers of sample numbers 21 to 23.

On the other hand, sample numbers 22 and 23 were, since the reaction temperature was as high as 200 to 250° C., also high in crystallinity, and with grain growth promoted, 6.1 to 8.0 nm in average grain diameter Dav, and also 1.2 to 2.5 nm in standard deviation σ. It has been determined that favorable emission characteristics are obtained, also with the half-value width from 72 to 82 nm in the wavelength range of 820 to 890 nm, and a steep curve drawn by the emission intensity.

For comparison, sample number 22 was 52 nm in Stokes shift, whereas sample number 21 was as large as 200 nm in Stokes shift.

EXAMPLE 4

A sample of sample number 31 was prepared by the same method and procedure as for sample number 3, except that n-octyl ether with a purity of 95% (manufactured by Tokyo Chemical Industry Co., Ltd.) was used as a high boiling point solvent, instead of 1-octadecene, and that the reaction time was adjusted to 120 minutes.

Next, for each sample of sample number 31, an emission spectrum, an absorption spectrum, and a quantum yield were determined by the same method and procedure as in Example 1, and the peak wavelength, the half-value width, and the absorption coefficient were determined from the emission spectrum and the absorption spectrum, and furthermore, the Stokes shift S was obtained from the peak wavelength and the absorption coefficient.

Figure 14:
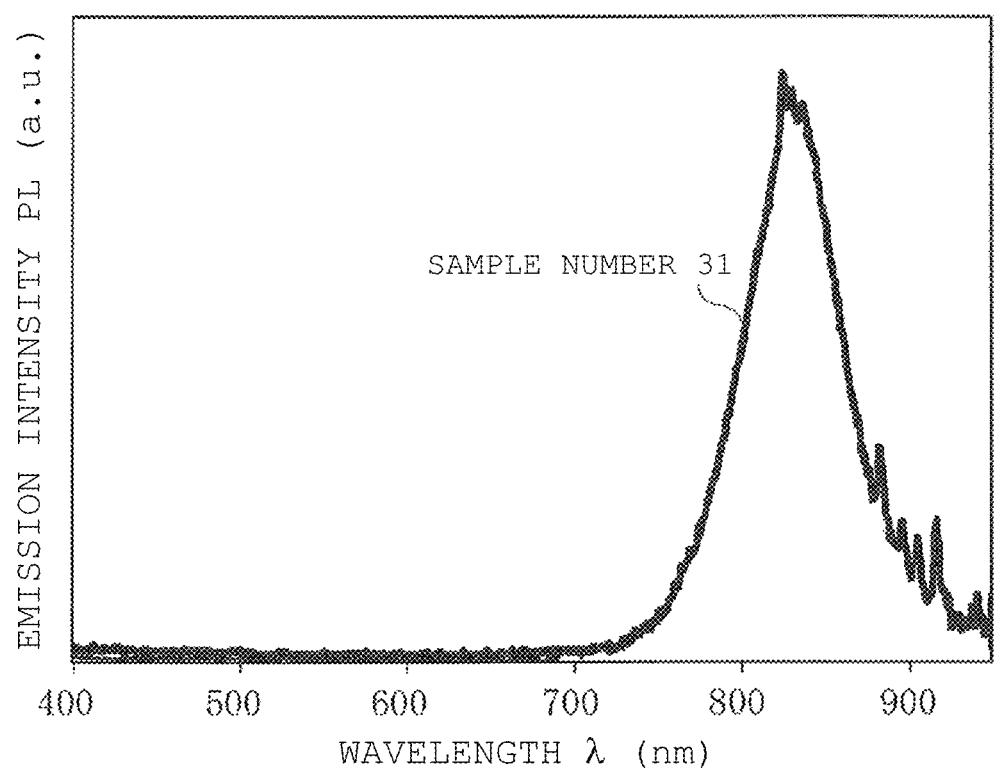
FIG. 14 is a diagram showing an emission spectrum according to Example 4.

FIG. 14 shows the emission spectrum of sample number 31, where the vertical axis indicates an emission intensity PL (a.u.), whereas the horizontal axis indicates a wavelength λ (nm).

As is clear from FIG. 14, the peak wavelength of the emission intensity was about 830 nm, and the half-value width was 65 nm. In addition, with the quantum yield of 14% and the Stokes shift of 54 nm, it has been determined that a light emitter which has substantially the same favorable emission characteristics as sample number 3 is obtained even when the type of the high boiling point solvent is changed.

COMPARATIVE EXAMPLE

AgInS$_2$ was prepared with the use of S instead of Se in AgInSe$_2$, and the emission spectrum and the absorption

TABLE 2

| Sample No. | Reaction Temperature (° C.) | Half-Value Width (nm) | Average Grain Diameter Dav (nm) | Standard Deviations σ (nm) | Peak Wavelength (nm) | Emission Spectrum | TEM IMAGE |
|---|---|---|---|---|---|---|---|
| 21* | 150 | >100 | 4.7 | 0.8 | 880 | FIG. 8 | FIG. 11 |
| 22 | 200 | 82 | 6.1 | 1.2 | 820 | FIG. 9 | FIG. 12 |
| 23 | 250 | 72 | 8.0 | 2.5 | 890 | FIG. 10 | FIG. 13 |

*outside the scope of the present disclosure.

Sample number 21 was 880 nm in peak wavelength, but greater than 100 nm in half-value width. This is believed to be because the reaction temperature was as low as 150° C., thus leading to low crystallinity, generating many defects in the crystal grains, causing an energy loss derived from the defect levels, as a result, making the peak wavelength of the emission intensity gentle, and thus failing to obtain any steep peak wavelength.

spectrum were each measured, and the Stokes shift was obtained, evaluating the emission characteristics.

More specifically, 0.1 mmol of Ag(OCOCH$_3$), 0.1 mmol of In(OCOCH$_3$)$_3$, and 0.2 mmol of CH$_4$N$_2$S (thiourea) were each weighed, and the weighed material was poured together with a stirrer chip into a test tube of 16 mm in inner diameter and of 180 mm in total length. Then, a mixed solvent of 2.95 mL of oleylamine and 0.05 mL of 1-dodecanethiol was poured into the test tube, the test tube was then closed with a double cap, the inside of the test tube was degassed under reduced pressure and purged with nitrogen, and thereafter, the test tube was placed on a hot stirrer heated to 250° C., and heated for 10 minutes. Thereafter, as in Example 1, air-cooling, centrifugation, and the like were carried out for cleaning and purification, and the obtained ultrafine particles of $AgInS_2$ were then dispersed in chloroform to prepare a sample composed of an $AgInS_2$ nanoparticle dispersion solution according to a comparative example.

Then, the emission spectrum, the absorption spectrum, the quantum yield, the half-value width, and the Stokes shift were determined by the same method and procedure as in Example 1.

Figure 15:
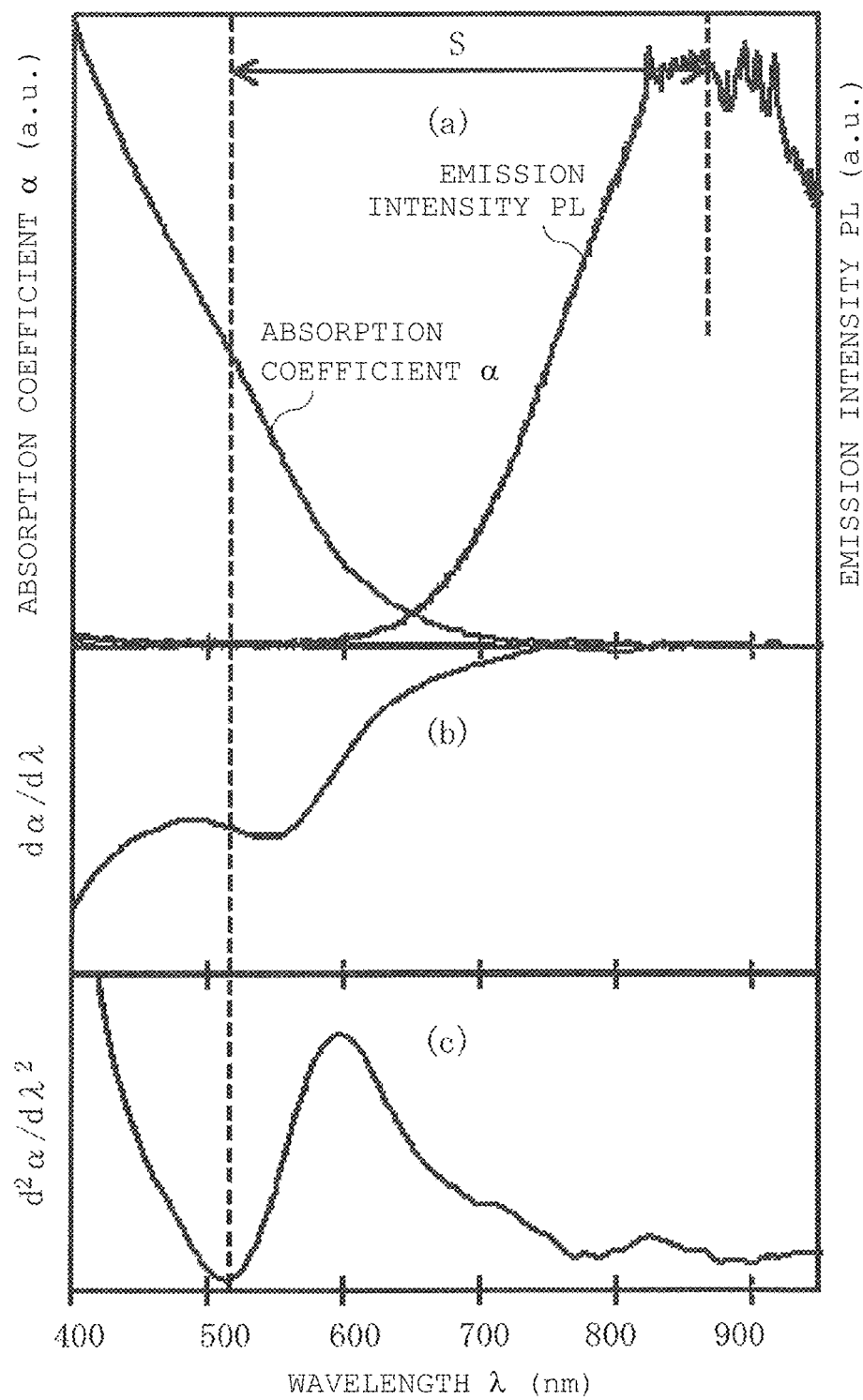
FIG. 15 is a profile showing the relationship among an emission spectrum, an absorption spectrum, and a Stokes shift according to a comparative example.

FIG. 15 is a profile showing the measurement results.

More specifically, as shown in section (a) of FIG. 15, the emission spectrum and the absorption spectrum for the sample according to the comparative example, where the horizontal axis indicates a wavelength λ (nm), the left vertical axis indicates an absorption coefficient α (a.u.), and the right vertical axis indicates an emission intensity PL (a.u.).

As shown in section (b) of FIG. 15, a profile of a derivative dα/dλ for the sample according to the comparative example, where the horizontal axis indicates a wavelength λ (nm), whereas the vertical axis indicates a derivative dα/dλ.

As shown in section (c) of FIG. 15, a profile of a second order derivative $d^2α/dλ^2$ for the sample according to the comparative example, where the horizontal axis indicates a wavelength λ (nm), whereas the vertical axis indicates a second order derivative $d^2α/dλ^2$.

While the quantum yield of the sample according to the comparative example was as high as 52%, the half-value width of the sample was about 200 nm, with an emission peak in a wide wavelength range, as is clear from FIG. 15, thus failing to obtain a steep emission peak. In addition, the Stokes shift S is also as large as 351 nm, and luminescence derived from the defect levels is believed to be produced.

Thus, in view of the foregoing disclosure, a light emitter is provided that is configured to emit strong light with a small half-value width αH in the near-infrared region of 700 to 1400 nm. As such, a biological substance labeling agent is disclosed that is suitable for a biomarker in bioimaging.

The invention claimed is:

1. A light emitter for labeling a biological substance, the light emitter comprising:
    nanoparticles composed of a compound semiconductor that contains an Ag compound, an In component, and a Se component,
    wherein the compound semiconductor is a light-emitting material that emits light at an emission intensity having a peak wavelength within a range between 700 nm and 1400 nm, and
    wherein a mixing ratio of the In component to the Ag component is between 2 and 3 in terms of molar ratio, such that the light-emitting material is constructed to emit light at the emission intensity having the peak wavelength that is 85 nm or less in half-value width.

2. The light emitter according to claim 1, wherein the peak wavelength is between 700 nm and 1000 nm.

3. The light emitter according to claim 1, wherein the compound semiconductor contains the In component in excess with respect to the stoichiometric composition of the compound semiconductor.

4. The light emitter according to claim 1, wherein the emitted light comprises an absorption wavelength with at least a portion between 700 nm and 1000 nm.

5. The light emitter according to claim 1, wherein the compound semiconductor has an average particle size between 0.1 nm and 20 nm.

6. A biological substance labeling agent comprising the light emitter according to claim 1.

* * * * *